United States Patent [19]

Feferman et al.

[11] Patent Number: 5,952,275
[45] Date of Patent: Sep. 14, 1999

[54] GLYCERIN LIQUID SOAP WITH A HIGH MOISTURIZING EFFECT

[75] Inventors: Israel Henrique Stokfisz Feferman; Mauricio Cella E. Santos; Silvana Masiero, all of Sao Paulo, Brazil

[73] Assignee: Johnson & Johnson Consumer Products, Inc., Skillman, N.J.

[21] Appl. No.: 08/820,515

[22] Filed: Mar. 19, 1997

[51] Int. Cl.⁶ ..................................................... A61K 7/50
[52] U.S. Cl. ........................... 510/130; 510/159; 510/407; 510/495; 510/461; 424/401
[58] Field of Search ...................... 510/130, 159, 510/407, 461, 495; 424/401

[56] References Cited

U.S. PATENT DOCUMENTS

| | | | |
|---|---|---|---|
| 4,263,284 | 4/1981 | Schreuder | 510/159 |
| 4,312,771 | 1/1982 | Matsuda | 510/159 |
| 4,420,410 | 12/1983 | Huttinger | 510/159 |
| 4,976,953 | 12/1990 | Orr et al. | 510/159 |
| 5,002,680 | 3/1991 | Schmidt et al. | 510/159 |
| 5,130,056 | 7/1992 | Jakobson et al. | 510/159 |
| 5,188,756 | 2/1993 | Baker | 510/159 |
| 5,234,619 | 8/1993 | Greene et al. | 510/159 |
| 5,308,526 | 5/1994 | Dias et al. | 510/159 |
| 5,496,492 | 3/1996 | Hamada et al. | 510/159 |

*Primary Examiner*—Jacqueline V. Howard

[57] ABSTRACT

This invention relates to a liquid composition for personal cleansing and hydrating of human skin containing a cleaning agent such as an anionic, amphoteric or non-ionic surfactant, and a hydrating agent such as glycerol. The compositions of this invention substantially block transepidermal water loss.

1 Claim, No Drawings

GLYCERIN LIQUID SOAP WITH A HIGH MOISTURIZING EFFECT

BACKGROUND OF THE INVENTION

The present invention refers to compositions for personal cleaning and hygiene, especially hydrating toilet soaps, comprising a system balanced with cleaning and hydrating agents. Advantageously, the compositions of this invention have a suave action on the eyes and skin, and are biodegradable.

In a more specific way, without excluding other embodiments, the compositions of the present invention are in liquid form, that is to say, they are easy and pleasant to use, being also adaptable to be employed in flexible tubes, commercial, household and hospital dispensers, and the like.

Unexpectedly, the use of the compositions of the invention is intended for washing and personal body hygiene, besides skin and hair cleaning, effective skin hydration unlike a feeling of hydration created, for instance, by occlusive products, which only prevent water from draining out of the skin, as widely known in the prior art.

The compositions of the present invention provides, in an unusual manner, personal cleaning and hygiene, effective skin, hydration, a good foaming, biodegradability and a suave action on the skin and eyes, which makes its use advantageous for children and people having sensible skin.

Under normal conditions, the human health skin is covered by a layer of fatty substances which actuate as a barrier against aggressions from the environment. Within a dynamic balance with the moistness of this environment, such a barrier allows the water contained therein to evaporate to some extent.

During the washing, in contact with either soap or detergent substances in general, this superficial layer is partly removed, whereby the evaporation rate increases, thus causing the skin to dry up. Further as a result of the removal of the superficial fatty layer, there is the direct action of the components of the formulation of soap or detergents on the skin, often causing redness, wrinkling and even wounds in cases of greater sensitivity and/or long exposition.

The technique itself of using compositions for personal cleaning and hygiene, namely the washing, favors the drying of the skin, that is to say, one spreads and rubs the composition on the skin with some water, forming foam, and then rinses it with running water. Under these conditions, the superficial fatty material is removed by the rinsing water together with the cleaning product, thus leaving the washed surface unprotected. Therefore, even toilet soaps having high glycerin or polyol contents, which are traditionally considered hydrating substances, have not succeeded in preventing the skin from becoming dryer and more sensible, because they do not remain on the skin.

It is well known that the addition of emollient substances to personal cleaning compositions aims at mitigating such effects of drying and sensibility, but the use thereof is compulsorily limited, because they are antifoaming and do not actually cause hydration.

This kind of problem does not occur with lotions, creams and other products intended especially for hydrating the skin, since they are applied onto the skin and remain thereon in prolonged contact. Therefore, they are not products such as those of the present invention, which are also intended for body cleaning and hygiene.

The compositions of the invention manage to combine in an unusual way the simultaneous action of cleaning and hydrating the skin effectively, through a balanced system of cleaning and hydrating agents, which, in the face of the prior art, could not be regarded as presenting such properties. In addition, a cosmetically acceptable foaming, a suave action on the skin and eyes and biodegradability are obtained.

The prior art mentions formulations of products for personal cleaning and hygiene, but they are different from the present invention, namely:

Patent Document E 0330369 discloses skin-conditioning liquid compositions, based on silicone emulsions and high glycerine contents, which are spread over the skin so as to form a superficial layer, in order to be effective. This type of product, different from that of the invention, is not intended for skin cleaning.

Patent Documents GB 1427341 and GB 20057297 disclose the composition of a creamy toilet soap having high glycerin contents (maximum of 50% and 20% respectively) for personal washing, which aims at preventing the composition from drying at the discharge nozzle of the dispenser and providing it with storage stability. This document does not seek or foresee that effective hydration of the skin will take place through the use of the disclosed soap.

U.S. Pat. No. 4,312,771 discloses a liquid soap composition containing form 9 to 11 parts by weight of glycerine and/or glycol propylene such that the quite stable viscosity obtained will always be the highest possible at room temperature. The formulation disclosed simultaneously does not seek or foresee that effective skin hydration occurs.

Patent Document No. E 0,485,212 discloses a liquid detergent composition for personal washing comprising up to 15% hydrating agent (for example, glycerol), which aims at obtaining from in an adequate amount, in spite of the presence of emollients mentioned as being intrinsically antifoaming. The formulation disclosed do not seek or foresee that effective skin hydration will occur.

In view of the non-existence of a composition for simultaneous personal cleaning and hygiene with effective hydration effect in the prior art, the present invention has been developed, which deals with compositions for personal cleaning and hygiene, characterized by comprising a cleaning agent and a hydrating agent in a balanced combination and by providing a value of transepidermal water loss approximately equal or lesser than that of the skin per se.

The measurement of transepidermal water-vapor loss (TEWL) allows one to stimulate the water flow through the stratum corneum of the skin, and this technique has been widely used for determining the barrier function of the skin against the aggressin of detergents and evaluating body cleaning products, especially as regards hydration. The publications mentioned below illustrate, by way of non-limiting example, the above statements:

Finkaj, M. D. and Crowe, D. M., "The use of Evaporimetry to Evaluate Soap Induced Irritation on the Face." "Skin", 4, 311–321 (1988);

Kajs, M. T. and Gartstein, V. "Review of the Instrumental Assessment of Skin: Effects of Cleansing Products" J. Soc.Cosm. 42, 249–271 (1991);

Wilson, D., Berardesca, E. and Maiach, H. I. "In-vivo Trans-epidermal Water Loss and Skin Surface Hydration in Assessment of Moisturization and Soap Effects." J.Cosm. Sci. 10(5), 201–211 (1988);

Rothman, S. "Physiology and biochemistry of the Skin". The University of Chicago Press, Chicago (1954);

Leveque, J. L., Garson, J. C. and de Rigal, J. "Trans-epidermal Water Loss From Dry and Normal Skin" J. Soc. Cosm.Chem. 30, 333 (1979);

Van de Valg, P. G. M., Nater, J. P. and Belumink, E. "Skin Irritance of Surfactants as Assessed by Water Vapor Loss measurements." J. of Invest. Dermatol. 82(3) 291–293 (1984);

Batt, M. D. and Fairhurst, E. "Hydration of the Stratum Corneum. Int." J. Cosm.Sci. 8, 253–264 (1986).

The cleaning agent used in the present invention comprises a surfactant, either in isolation or in combination with an emollient agent.

Surfactants, emollients and hydrating agents, mentioned as being components of the compositions of the present invention, are in solution products known to those skilled in the art, and information about them can be found, for instance, in publications such as:

CTFA Cosmetic Ingredient Handbook—NIKITAKIS, J. M. Editor,—The Cosmetic, Toiletry and Fragrance Association Inc. USA—1st edition, 1988.

Harry's Cosmeticology—Winkinson, J. B. and Moore, R. J., Editors—Langman and Scientific and Technical, USA 7th Ed., 1982.

Unless otherwise stated, the percentages given below refer to the weight of the composition.

Preferably, the amount of the cleaning agent in the present invention is of from 9 to 19% by weight of the composition.

Advantageously the surfactant of the cleaning agent of the present invention is chosen from the anionic, amphoteric or non-ionic surfactants, preferably a mixture thereof. Within the composition of the invention the contents thereof may vary preferably from 9% to 19%, and more preferably range from 11 to 17% by weight of the composition. When a mixture of anionic, amphoteric and non-ionic surfactants is used, the percentages thereof, preferably can vary from about 2.5% to 5%, 3.5% to 7.0% and 5.5% to 11.0%, respectively, by weight of the composition.

Preferably, the anionic surfactants are chosen from the alkyl ether sulfates, the sulphosuccinates and the acylisothyanates, as for instance, triglyceryleter sodium sulphate.

Preferably, the amphoteric surfactants are chosen from the alkyl imidazolins and the alkyl aminoacids such as betaines, cocoamidopropylbetaine and cocoanphocarboxylglycinate.

Preferably the non-ionic surfactants are chosen from the alkanolamides and the polyethylene glycol derivatives, as for instance, polyethylene glycol laurate sorbitan, lauryl polyglycose and sodium carboxylate laurylether.

Ready-for-use compositions comprising the cited surfactants are available on the market.

The emollient agent, component of the cleaning agent of the present invention, can be defined as one or more ingredients that help to maintain the skin soft, suave and flexible. Preferably an amount ranging from about 0.5% to 10%, more preferably from 1.0% to 5% by weight of such a component is used, based on the weight of the composition.

Preferably the emollient agent is a mixture of etoxylated and propoxylated cetyl alcohol and ethoxylated lanolin.

The hydrating agent of the present invention is preferably chosen from the list made up of polyhydric alcohols (for example, glycerol, sorbitol, mannitol, xylitol, polyethylene glycol, 1,2,6-hexanotriol, inositol), alkylene glycols (for example 1.3-buthylene glycol, diethylene glycol, triethylene glycol) and derivatives of the glutamic acid (for example, sodic pyroglutanate) or mixtures thereof. More preferably, the hydrating agent is either glycerol or sorbitol, either individually or in mixture with each other or with one or more hydrating agents. Also preferably the contents of the hydrating agent in the compositions of the invention range from 5% to 25%, more preferably from about 18% to 23% by weight of the composition.

Carriers such as water can be used in the compositions of the invention in the amounts usually employed in the art. The use of such components as well as their specificity are well known by those skilled in the branch of the compositions of the present invention.

The compositions of the invention can also contain, optionally, without departing from the scope of the invention, a wide variety of additives known by those skilled in the art, for instance perfumes, dyes, preserving agents, thickeners, opacifiers, antioxidants, hydrating agents, stabilizers, disinfectants, emulsifiers, etc., taking into account the additional specific needs or properties which one desires to reach.

EXAMPLE OF DETERMINING THE TEWL

The room tests are made over the volar region, or underside of the forearm, of the panelists. The distal volar region (region C) was the control region for non-treated skin and the proximal volar region (region T) was the region of application of the composition under test.

An amount of 4 g of product to be tested is applied to region T during 30 seconds, with light and circular movements, and then a careful rinsing with running water (2 liters/min) is made during 1 minute. This application cycle is repeated 4 times. The application place is dried with a light pressure of the absorbent paper. After eight minutes of rest of the panelist, readings of the value of the water-vapor flow is made each 2 minutes alternately at regions T and C. The difference between such readings is the TEWL value, given in $gm^{-2}h^{-1}$, which is plotted with respect to the time and shown in FIG. 2.

A PRACTICAL EXAMPLE OF THE INVENTION

In order to compare the invention with products of the prior art, the composition A described below has been formulated, and it TEWL values (as described previously) were compared with product available on the market such as the common bar toilet soap, based on coconut and tallow, and the bar toilet soap commercially called "Dove" (the latter is disclosed as containing 25 percent of hydrating cream).

In the "component" column the respective percentage is given by weight of specific active product in the respective formulation (solution) used, the percentages indicated in the "composition A" column being taken on the basis of the respective formulations.

| COMPONENT | FUNCTION | COMP. A |
|---|---|---|
| tridecylether sodium sulfate at 30% | anionic surfactant | 12.60 |
| cocoamidopropyl-betaine at 30% | amphoteric surfactant | 9.80 |
| cocoannfocarboxy-glycinate at 30% | amphoteric surfactant | 7.00 |
| polyethylene glycol laurate sorbitan at 72% | non-ionic surfactant | 6.80 |
| lauryl polyglycose at 50% | non-ionic | |
| sodium carboxylate laurylether at 70% | non-ionic | |
| ethoxylated and propoxylated cetyl alcohol at 100% | emollient | 2.00 |
| ethoxylated lanolin at 50% | hydrating agent | 20.00 |
| water | carrier | qsp 100 |

With the teachings of the prior art known so far, it would be possible to foresee that formulation A would provide a lesser increase in TEWL, that is to say a behavior similar to that obtained by the liquid toilet soap available commercially under the name "Neutrogena". However, one obtains a behavior indicating that hydration is taking place, since the other conditions of use of the product are maintained.

In order to establish the existence of hydration of the skin more surely, the electric resistance of the skin after application of formulation A was measured and the value obtained for non-treated skin was compared. It was found that the value obtained with formulation A (0.24 giga Ohms) was lower than that obtained for treated skin (0.26 giga Ohms), thus corroborating the existence of hydration.

The method utilized for determining the electric resistance of the skin is as follows:

a cotton disk of about 4 cm² in area, containing 0.8 g of the liquid toilet soap formulation of the invention is placed on a site of 4 cm² in the test volar region T of the panelist, as shown in FIG. 1, during 4 minutes. The cotton disk is removed and the region is rinsed with running water for 1 minute with water flow of 2 liters/min. The application of a new cotton disk containing liquid toilet soap, follows by washing, as described, is repeated several times, with rest interval of 40 minutes. After 30 minutes from the last application and rinsing, the panelist remains 30 minutes in an ambient climatized at 20° C. and average relative humidity of 45% when the electric resistance of the skin of site T and of site C of the non-treated skin is measured. For such measurement of the electric resistance of the skin, a Keythley 617 of the American Firm Keythley is used, connected to stainless steel electrodes, one being cylindrical, to be in contact with the panelist's gums, and the other disk with an area of about 3.8 cm² to be in contact with the skin of the desired region, under a pressure of about 23.7 g/cm².

Composition A was used in a practical test with 10 women at the age of from 30 to 50 years, during one week.

Composition A was used daily to wash one of the legs, while the usual toilet soap of the panelist was used on the rest of the body. In the beginning and at the end of the study the leg of each panelist was assessed, and the hydrating effect of the product was statistically significant.

What is claimed is:

1. A composition for personal cleansing and hydrating of human skin comprising:

| Component | Percent Actives | Percent in Formulation | Percent in Formulation (Actives Basis) |
| --- | --- | --- | --- |
| Sodium Trideceth Sulfate | 30 | 12.6 | 3.8 |
| Sodium Laureth Carboxylate | 70 | 1.0 | 0.7 |
| Cocamidopropyl Betaine | 30 | 9.8 | 2.9 |
| Cocoamphocarboxyglycinate | 30 | 7.0 | 2.1 |
| PEG Sorbitan Laurate | 72 | 6.8 | 4.9 |
| Lauryl Polyglucose | 50 | 3.4 | 1.7 |
| Propoxylated Ethoxylated Cetyl Alcohol | 100 | 2.0 | 2.0 |
| Ethoxylated Lanolin | 50 | 3.0 | 1.5 |
| Glycerol | 100 | 20.0 | 20.0 |

* * * * *